(12) United States Patent
Chou et al.

(10) Patent No.: US 7,230,716 B2
(45) Date of Patent: Jun. 12, 2007

(54) METHOD FOR MEASURING THE ABSORPTION COEFFICIENT AND THE REDUCED SCATTERING COEFFICIENT OF A MULTIPLE SCATTERING MEDIUM

(76) Inventors: Chien Chou, 5F, No. 37-3, Chuan-Yuan Rd., Pei-Tou Dist., Taipei City (TW); Yi-Shin Chan, 5F, No. 37-3, Chuan-Yuan Rd., Pei-Tou Dist., Taipei City (TW); Jheng-Syong Wu, 5F, No. 37-3, Chuan-Yuan Rd., Pei-Tou Dist., Taipei City (TW)

( * ) Notice: Subject to any disclaimer, the term of this patent is extended or adjusted under 35 U.S.C. 154(b) by 442 days.

(21) Appl. No.: 10/763,655

(22) Filed: Jan. 23, 2004

(65) Prior Publication Data

US 2005/0162660 A1    Jul. 28, 2005

(51) Int. Cl.
*G01B 9/02*    (2006.01)
(52) U.S. Cl. ...................... 356/484; 356/491
(58) Field of Classification Search ................ 356/484, 356/485, 486, 487, 491, 492, 493
See application file for complete search history.

(56) References Cited

U.S. PATENT DOCUMENTS

| | | | |
|---|---|---|---|
| 5,428,447 A * | 6/1995 | Toida ........................ | 356/601 |
| 6,327,037 B1 | 12/2001 | Chou et al. | |
| 6,526,298 B1 * | 2/2003 | Khalil et al. ................ | 600/310 |
| 2001/0028679 A1 | 10/2001 | Chou | |

OTHER PUBLICATIONS

Advanced Biomedical and Clinical Diagnostic Systems, Tuan Vo-Dinh, Warren S. Grundfest, David A. Brenaron, Gerald E. Cohn, Editors, Proceedings of SPIE vol. 4958 (2003), pp. 259-272, The measurement of optical properties of a multiple scattering medium based on diffused photon pair density wave, Yi-Hsin Chan et al.
Applied Optics, Jul. 1, 2001, vol. 41, No. 19, pp. 3827-3839, Quantitative oximetry of breast tumors: a near-infrared method that identifies two optimal wavelengths for each tumor, Erica L. Heffer et al.
Applied Optics, Apr. 1, 1998, vol. 37, No. 10, pp. 1982-1989, Assessment of the size, position, and optical properties of breast tumors in vivo by noninvasive optical methods, Sergio Fantini et al.

* cited by examiner

*Primary Examiner*—Gregory J. Toatley, Jr.
*Assistant Examiner*—Michael A. Lyons

(57) ABSTRACT

In a method for measuring absorption and reduced scattering coefficients of a multiple scattering medium, a coherent light beam is outputted. The coherent light beam includes linear polarized P and S wave components having mutually orthogonal polarizations and frequencies $\omega P$ and $\omega S$, respectively. Then, the coherent light beam is split into a signal beam and a reference beam, which include the P wave and S wave components. The signal beam is subsequently projected into the medium. Optical interference signals of the reference beam and the signal beam penetrating the medium are respectively detected and converted into heterodyne interference electrical signals. Thereafter, the two heterodyne interference electrical signals are compared to obtain amplitude attenuation and phase delay of the signal beam penetrating the medium, from which the absorption and reduced scattering coefficients of the medium at a position where the signal beam penetrated the medium are inferred.

9 Claims, 6 Drawing Sheets

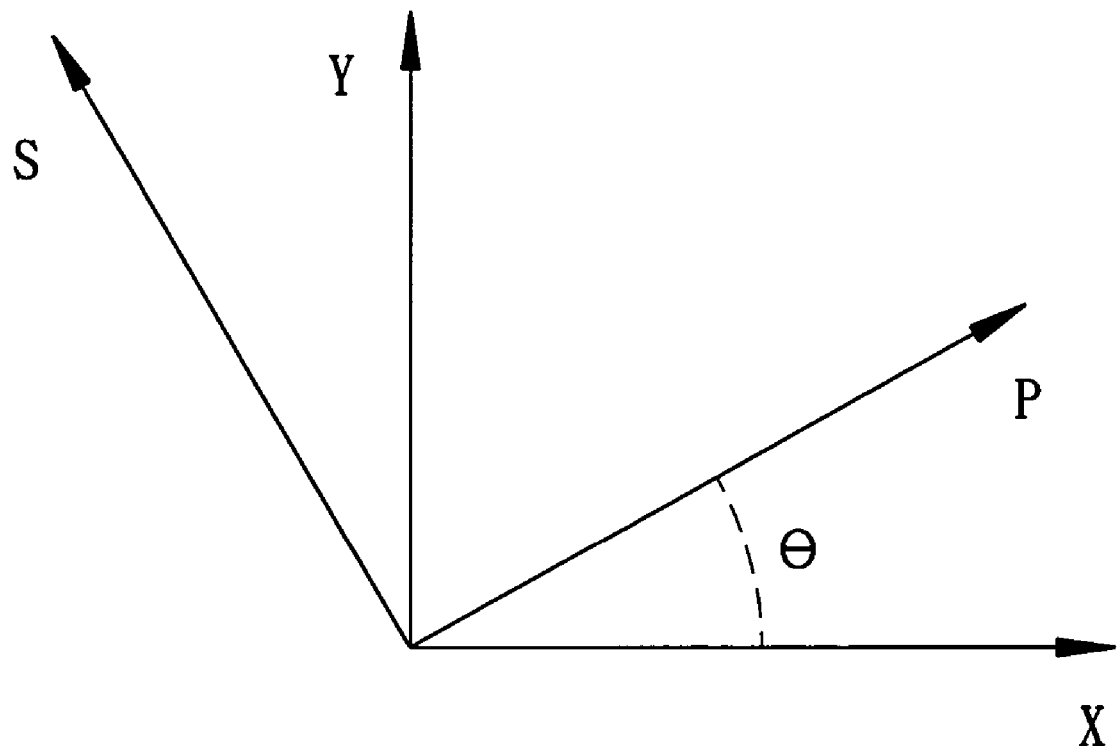
F I G. 5

METHOD FOR MEASURING THE ABSORPTION COEFFICIENT AND THE REDUCED SCATTERING COEFFICIENT OF A MULTIPLE SCATTERING MEDIUM

BACKGROUND OF THE INVENTION

1. Field of the Invention

The invention relates to a method for measuring the absorption coefficient and the reduced scattering coefficient of a medium, more particularly to a method for measuring in real time the absorption coefficient and reduced scattering coefficient of a multiple scattering medium.

2. Description of the Related Art

Human tissue is a highly scattering medium, and has the characteristics of having a scattering coefficient much greater than the absorption coefficient thereof. A conventional method of obtaining an image in a scattering medium involves measuring of absorption coefficients so as to obtain an image with contrast. However, when it is desired to obtain the image of an object in a multiple scattering medium, since the light waves are highly scattered, the resultant image is blurred, and the resolution of the image is also reduced considerably. Therefore, if the scattering effect of light in a relatively high scattering medium can be reduced, or if only slightly scattered snake photons and ballistic photons are selected, together with enhancement of the sensitivity to absorption coefficients, the resolution of an image in the medium can be enhanced. However, this is not suitable for imaging objects in multiple scattering media.

At present, methods for imaging in a multiple scattering medium mainly include time-domain and frequency-domain imaging techniques. The concept of diffused photon density wave (DPDW) is proposed in the frequency-domain technique. DPDW satisfies the diffusion equation, and can be relied upon to obtain definite amounts of the absorption and scattering coefficients of the test object, thereby permitting recovery of the image of an object in the scattering medium. The frequency-domain technique is currently more suitable for imaging in a multiple scattering medium, but has the drawback that the spatial resolution is not high. Thus, how to enhance imaging resolution in applications that involve a multiple scattering medium is currently an important topic in the industry.

SUMMARY OF THE INVENTION

A two-frequency polarized laser, e.g., a Zeeman He-Ne laser, can produce a two-frequency mutually correlated and mutually orthogonal linear polarized photon pair (PPP) laser beam for propagation through a highly concentrated scattering medium to produce a diffused polarized photon pair density wave (DPPDW). Particularly, by means of a polarizer, the mutually correlated and mutually orthogonal linear polarized photon pair can be effectively converted into a mutually correlated and mutually parallel polarized photon pair. The present invention primarily contemplates the propagation of a mutually correlated and mutually parallel two-frequency polarized photon pair in a multiple scattering medium to form a diffused polarized photon pair density wave while satisfying the diffusion equation. The same result can be achieved if a two-frequency circular polarized photon pair is converted into a mutually parallel polarized photon pair by the use of a polarizer. By measuring directly the amplitude and phase of the DPPDW, the absorption coefficient $\mu_a$ and the reduced scattering coefficient $\mu_s'$ of the multiple scattering medium can be measured in real time, in which $\mu_s' = \mu_s(1-g)$, where $\mu_s$ is the scattering coefficient, and g is the scattering anisotropic parameter of the multiple scattering medium. The three-dimensional (3-D) distributions of $\mu_s'$ and $\mu_a$ are obtained by finding the solution to the diffusion equation so as to obtain optical characteristics of and images in the multiple scattering medium. Further, as oxyhemoglobin (HbO$_2$) and deoxyhemoglobin (Hb) have different absorption coefficients with respect to the same wavelength, by using a two-frequency laser source (preferably, two two-frequency lasers) having different center wavelengths, the hemoglobin saturation (S$_a$O$_2$) in blood can be measured in real time, and images of hemoglobin saturation distribution can also be obtained.

This invention provides a method using a two-frequency, two-polarization laser beam for propagation in a highly concentrated scattering medium so as to form DPPDW. Through optical heterodyne interference techniques and coherence of the polarized photon pair, the magnitude of the phase and amplitude of the DPPDW can be obtained from the heterodyne interference signals, and the absorption coefficient $\mu_a$ and the reduced scattering coefficient $\mu_s'$ of the scattering medium can be calculated from the phase delay and amplitude attenuation that change with the distance between a laser source and a photo detector.

The object of this invention is to provide a method for measuring the absorption coefficient and the reduced scattering coefficient of a multiple scattering medium, in which, due to coherence of a polarized photon pair, and processing with the use of a heterodyne polarized interferometer, scattering of a light beam by the medium can be reduced, thereby enhancing resolution.

Another object of this invention is to provide a spatial imaging method, in which, by changing measuring positions and recording the measurement results at each of the measuring positions, a complete image of the multiple scattering medium can be constructed.

According to the present invention, the method for measuring the absorption coefficient and the reduced scattering coefficient of a multiple scattering medium includes: outputting a coherent light beam, the coherent beam including linear polarized P and S wave components having mutually orthogonal polarizations and frequencies ωP and ωS, respectively; splitting the coherent light beam into a signal beam and a reference beam, the signal beam and the reference beam including the P wave and S wave components; projecting the signal beam into the multiple scattering medium; detecting and converting an optical interference signal of the reference beam and an optical interference signal of the signal beam that penetrates the multiple scattering medium and a polarizer, respectively, into heterodyne interference electrical signals; comparing the two heterodyne interference electrical signals to obtain amplitude attenuation and phase delay of the signal beam that penetrated the multiple scattering medium; and inferring the reduced scattering coefficient and the absorption coefficient of the multiple scattering medium at a position where the multiple scattering medium is penetrated with reference to the amplitude attenuation and phase delay thus obtained.

BRIEF DESCRIPTION OF THE DRAWINGS

Other features and advantages of the present invention will become apparent in the following detailed description of the preferred embodiment with reference to the accompanying drawings, of which:

FIG. 5 illustrates how P wave and S wave components are adjusted using a $$\frac{\lambda}{2}$$

Figure 4:
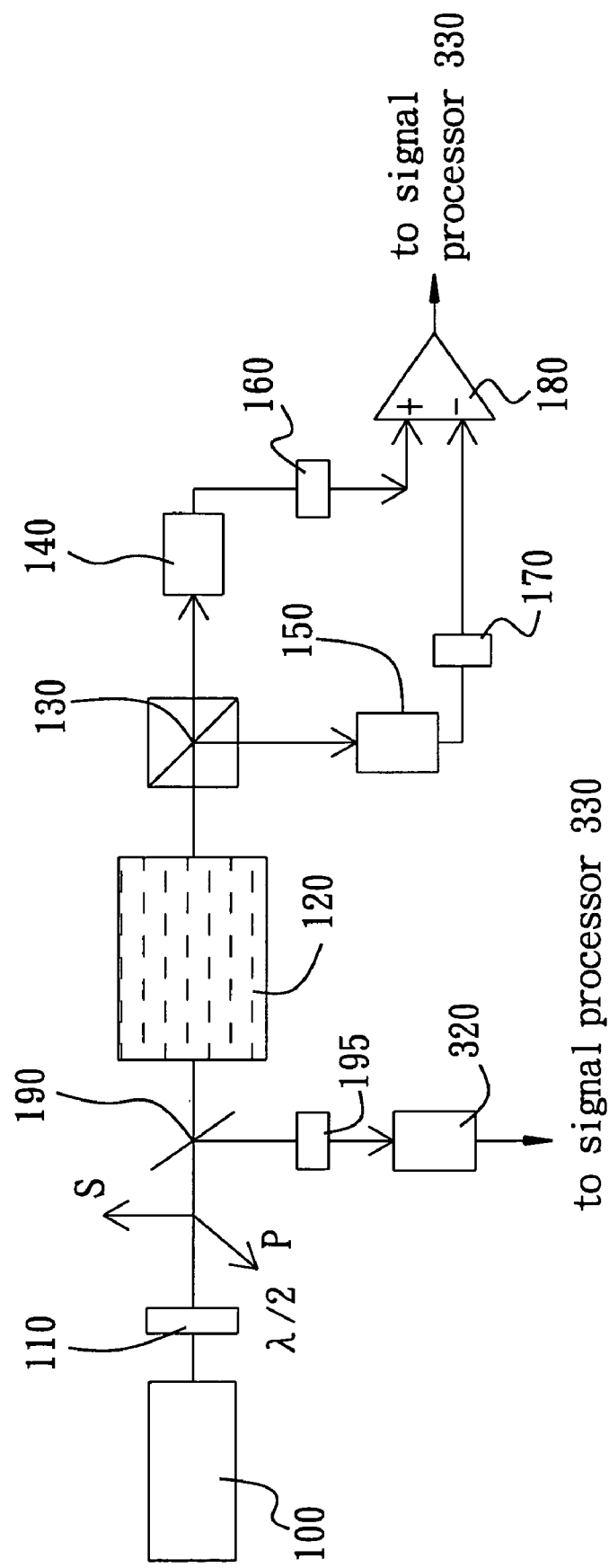
FIG. 4 is a block diagram of another apparatus for implementing the preferred embodiment.

wave plate in the apparatus of FIG. 4; and

Figure 6A:
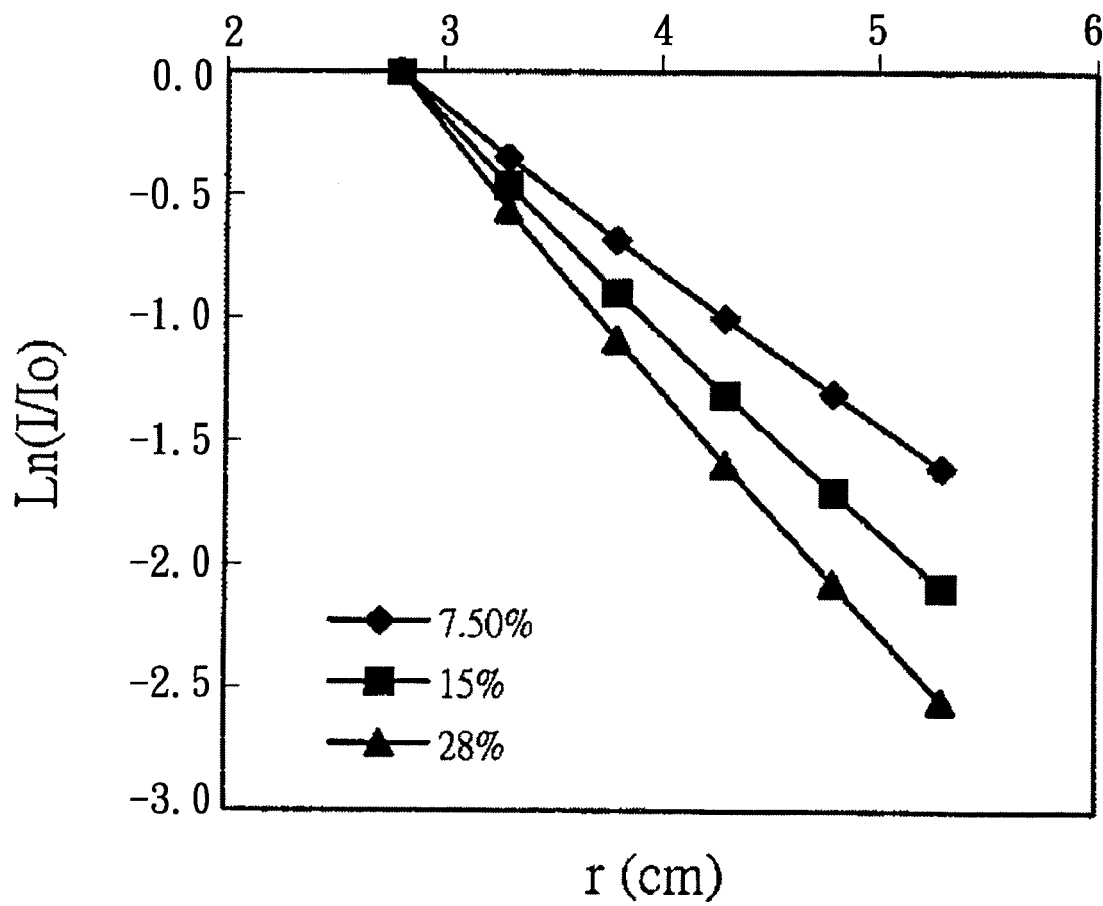
Figure 6B:
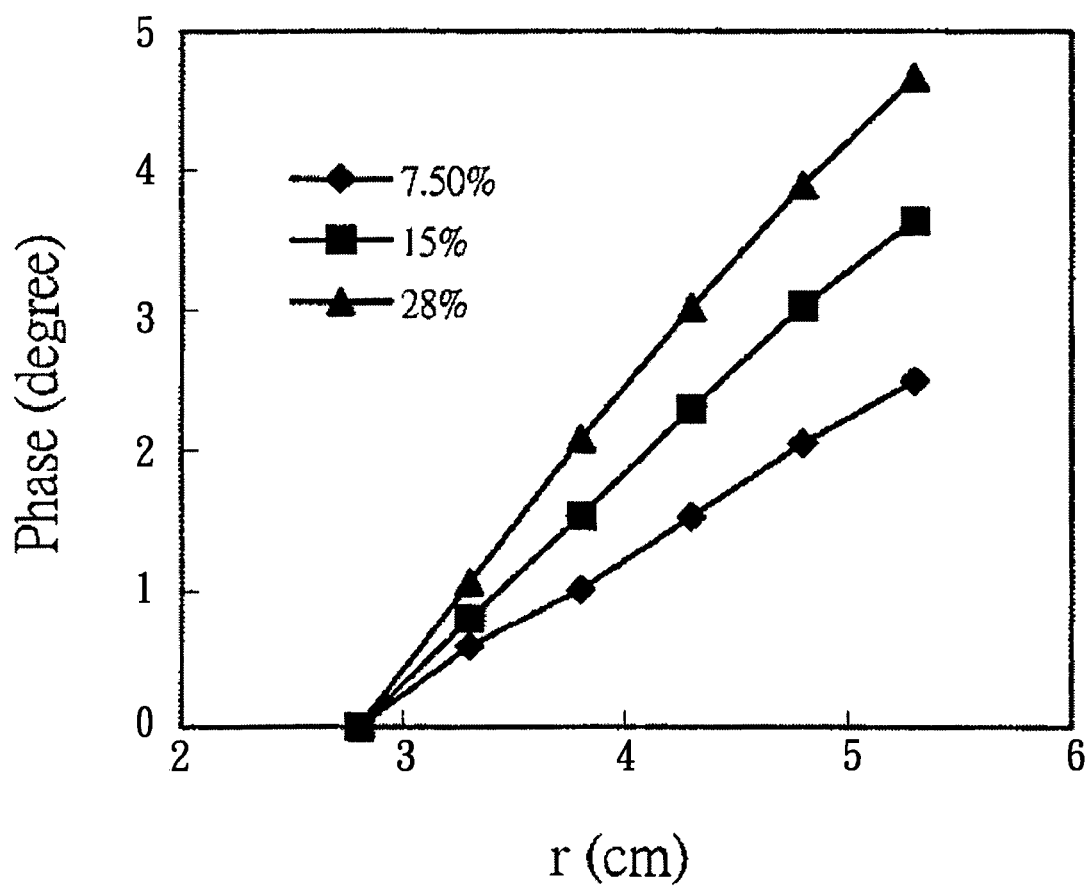

FIGS. 6A and 6B respectively illustrate the variation in amplitude attenuation and phase delay of DPPDW obtained in an experiment conducted by the applicant.

DETAILED DESCRIPTION OF THE PREFERRED EMBODIMENT

Figure 1:
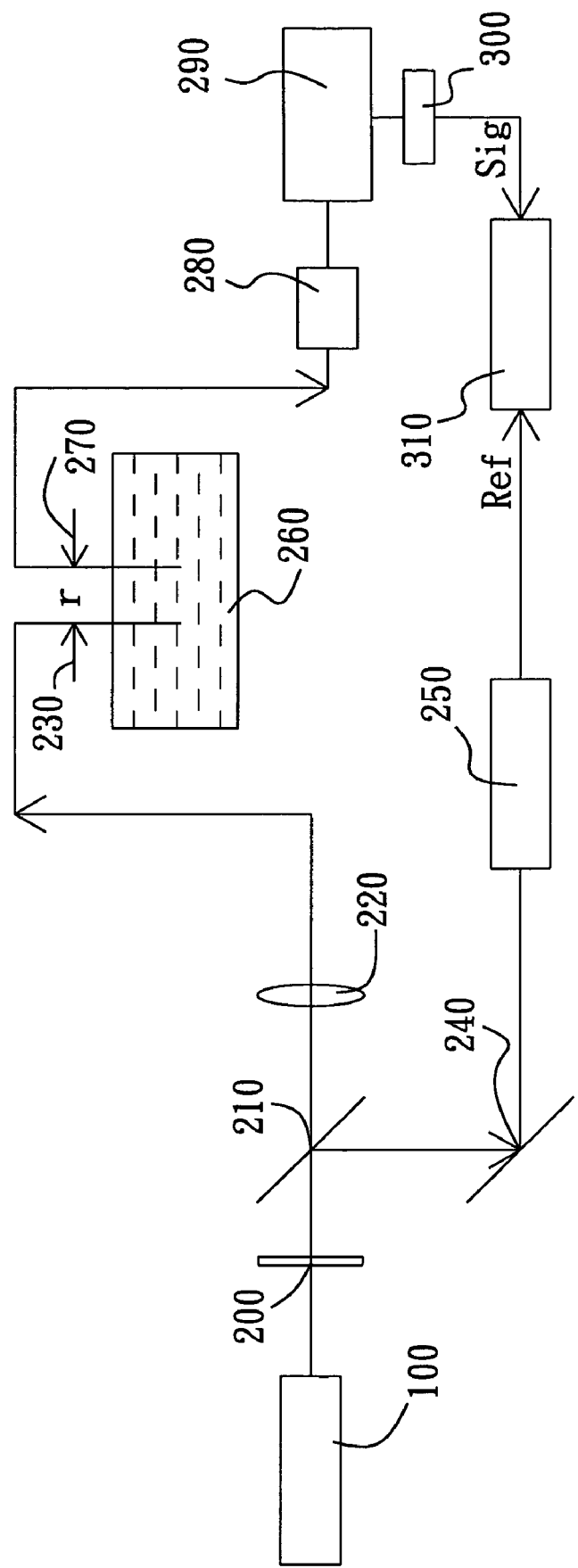
FIG. 1 is a block diagram showing the construction of an apparatus for implementing a preferred embodiment of a method according to the invention.
Figure 2:
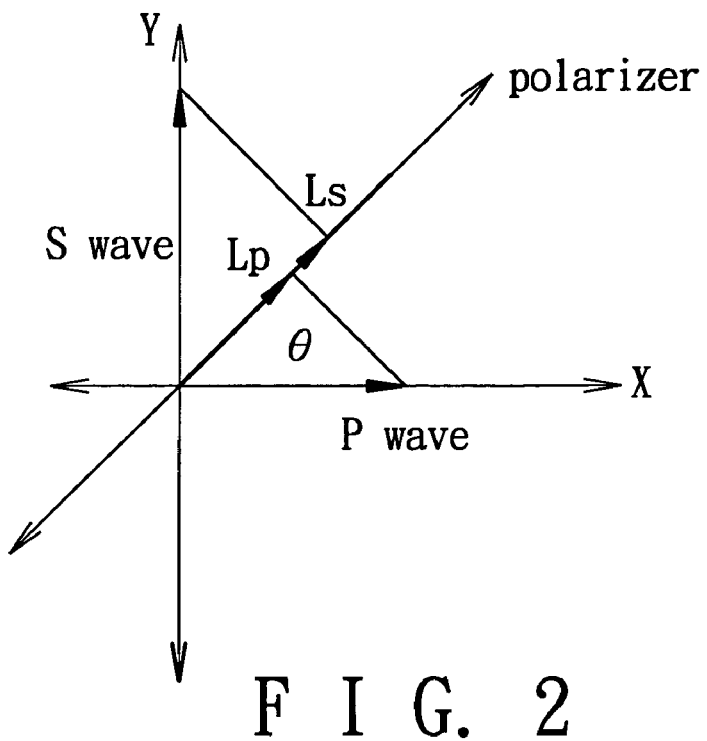
FIG. 2 is a schematic view illustrating the principle of generating a photon pair with parallel polarization directions in the apparatus of FIG. 1.

Referring to FIG. 1, a two-frequency, two-polarization laser 100, such as a Zeeman laser, outputs a coherent light beam, which includes mutually correlated and mutually orthogonal linear polarized waves that include a P wave and an S wave, the temporal frequencies of which being $\omega_p$ and $\omega_s$, respectively. The coherent light beam is passed through a polarizer 200 having an azimuth angle θ with respect to an axis (X). As shown in FIG. 2, since the angle of polarization direction of the polarizer 200 relative to the P wave is θ, the component of the P wave projected in the polarization direction is $L_p=A_p \cos θ \exp(i\omega_p t)$, whereas the projected component of the S wave is $L_s=A_s \sin θ \exp(i\omega_s t)$, thereby generating a photon pair ($L_p$, $L_s$) with mutually parallel polarization directions, wherein $A_p$ and $A_s$ are the amplitudes of the P wave and S wave components, respectively. Thus, a two-frequency mutually correlated and mutually parallel linear polarized photon pair beam is generated accordingly.

A beam splitter 210 splits the linear polarized photon pair beam into a signal beam $I_s$ and a reference beam $I_r$. The signal beam $I_s$ is focused via a microscopic object lens 220 for optic-fiber input into a signal optical fiber 230. At the same time, the reference beam $I_r$ is sent via a reflecting mirror 240 into a photo detector 250 to generate heterodyne interference reference signals, which can be expressed as follows:

$$I_r(\Delta\omega t)=DC+\Gamma \cos(\Delta\omega t) \quad (1)$$

in which Γ is the magnitude of the amplitude of the heterodyne interference signal of the P wave component and the S wave component in the reference beam $I_r$.

On the other hand, the signal beam $I_s$ is outputted from the other end of the signal optical fiber 230, and diffuses into a multiple scattering medium 260 to form DPPDW. A detector fiber 270 similar to the signal optical fiber 230 is disposed in parallel at a separation distance (r) from the signal optical fiber 230 for detecting the DPPDW. In a photo multiplier tube (PMT) 280, the heterodyne interference signals are generated, which are outputted through a signal amplifier 290 and a band-pass filter 300 to an electrical signal processor 310 (e.g., a phase-lock amplifier) for amplitude and phase measurements.

During the aforesaid process, when the polarized photon pair with mutually parallel polarization directions of the signal beam $I_s$ enter into the multiple scattering medium 260, although the coherence and the degree of polarization (DOP) of most of the polarized photon pairs are decorrelated due to a series of collision events, during the process of detecting the optical interference signals, some of the polarized photon pairs can still maintain their correlation such that a meaningful heterodyne interference signal is generated, the main frequency of the interference electrical signal being $\Delta\omega=\omega_p-\omega_s$. Therefore, after filtering through the band-pass filter 300 having a center frequency of $\Delta\omega=\omega_p-\omega_s$, other irrelevant noise signal scan be clearly removed.

Since only those of the polarized photon pairs which undergo relatively less collision events during passage through the multiple scattering medium can preserve relatively more polarization characteristics and directionality (or spatial coherence) for generating the heterodyne interference signals, the heterodyne interference technique according to this invention can be employed to screen diffused polarized photon pairs with a relatively low degree of scattering to form DPPDW. At the same time, they can also satisfy the diffusion equation. When the photon pairs with mutually parallel polarization directions are projected into a highly concentrated multiple scattering medium 260 and subsequently undergo photo detection, the intensity of the heterodyne interference signals thus generated can be expressed as follows:

$$I_s(\Delta\omega t)=DC+\gamma \cos(\Delta\omega t+\Delta\Phi) \quad (2)$$

in which $\Delta\omega=\omega_p-\omega_s$ is the beat frequency of the heterodyne interference signal; γ is the amplitude of DPPDW; and ΔΦ is the phase delay. $\mu_s'$ and $\mu_a$ of the multiple scattering medium can be obtained from the phase delay and amplitude attenuation of DPPDW. Equation (2) can be further rewritten as:

$$I_s(\Delta\omega t) = \varphi_0^2 \frac{e^{-k_{2r}r}}{r}\text{Re}\{e^{i(\Delta\omega t+\Delta\Phi)}\} \quad (3)$$

in which $\phi_0^2$ is the rate of energy fluence of DPPDW; $k_{2r}$ is the real number portion of the wave number $k_2$ of DPPDW, $k_2=k_{2r}+ik_{2i}$; $i=\sqrt{-1}$; and $k_{2r}$ corresponds to the absorption and scattering characteristics of the signal beam in the multiple scattering medium.

$$k_{2r}=[3 \mu_a(\mu_s'+\mu_a)]^{1/2} \quad (4)$$

From Equation (3), different separation distances $r_0$ and r can be obtained, and $\Delta r=r-r_0$. The amplitude attenuation of the signal beam in the multiple scattering medium is:

$$\ln\left(\frac{I}{I_0}\right) = \left[\ln\left(\frac{r_0}{r}\right) - k_{2r}\Delta r\right] \quad (5)$$

in which ($I_0$,I) are the intensities of the heterodyne interference signals at ($r_0$,r), respectively. Similarly, ΔΦ is the phase delay and can be expressed as follows:

$$\Delta\phi = \frac{n\Delta\omega}{c}\left(\frac{3\mu_s'}{4\mu_a}\right)^{1/2} \cdot r = k_{2i}r \quad (6)$$

-continued $$k_{2i} = \frac{n\Delta\omega}{c}\left(\frac{3\mu'_s}{4\mu_a}\right)^{1/2} \quad (7)$$

in which $k_{2i}$ is the imaginary part of the wave number $k_2$ of DPPDW, which corresponds to the scattering and absorption characteristics of the multiple scattering medium. ($\mu'_s$, $\mu_a$) are, respectively, the reduced scattering coefficient and the absorption coefficient of DPPDW in the multiple scattering medium. n is the refraction index of the medium, and c is the speed of light. From Equations (4) and (7), the following equations are obtained:

$$\mu'_s = \frac{2ck_{2r}k_{2i}}{3n(\Delta\omega)} \quad (8)$$

$$\mu_a = \frac{n\Delta\omega}{2c}\left(\frac{k_{2r}}{k_{2i}}\right) \quad (9)$$

Therefore, the characteristics ($\mu'_s$, $\mu_a$) of the multiple scattering medium can be obtained from the amplitude attenuation and the phase delay of the heterodyne interference signals measured by the apparatus shown in FIG. 1.

Figure 3:
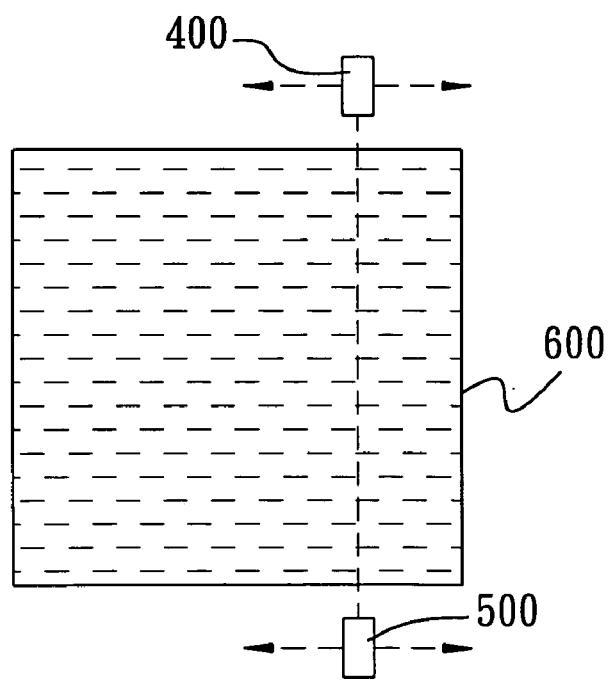
FIG. 3 is a schematic view of an imaging device employed in the preferred embodiment.

As shown in FIG. 3, a two-frequency laser source 400 and a detector 500 are displaced together relative to a multiple scattering medium 600 to perform two-dimensional (2-D) and three-dimensional (3-D) scanning. The spatial distribution of $\mu'_s$ and $\mu_a$ is obtained from the amplitude and phase data of DPPDW. Then, the diffusion equation is used to recover the object into an image. Details as to image recovery using the diffusion equation can be found in various literature, such as S. Fantini et al., "Assessment of the size, position, and optical properties of breast tumors in vivo by noninvasive optical methods," *Appl. Opt.* 37, 1982–1989 (1998); and E. L. Heffer et al., "Quantitative oximetry of breast tumors: a near-infrared method that identifies two optimal wavelengths for each tumor," *Appl. Opt.* 41, 3827–3839 (2002). The number of light sources and photo detectors can be adjusted suitably to obtain optimum imaging effects.

Certainly, as apparent to those skilled to the art, the two-frequency coherent light source can be achieved using various constructions. For instance, a linear polarized single-frequency stabilized laser is used to emit a polarized beam, and the polarization angle thereof is adjusted through a polarization angle adjusting device, such as a λ/2 wave plate. A polarized beam splitter splits the laser beam into orthogonal polarization directions, and both polarization laser beams are frequency shifted by passing through different frequency adjusting devices, such as acousto-optic modulators (AOM). Hence, the frequencies of the two beams with mutually orthogonal polarization directions can have a discernible minor frequency difference Δω). Then, the beams are integrated once again to become a two-frequency coherent beam that includes the P wave and the S wave. The frequency adjusting device may be an electro-optic modulator or any other similar device. Alternatively, by enabling a two-frequency laser with two different center wavelengths to undergo light synthesis, the polarized photon pair beam can also be projected into the multiple scattering medium by employing the aforesaid optical system so as to achieve a polarized photon pair for near-infrared spectroscopy (NIRS).

As shown in FIG. 4, in another apparatus for implementing the method of this invention, rotation of the azimuth angle through a $$\frac{\lambda}{2}$$

wave plate 110 can be used to adjust the azimuth angles of the P wave and S wave components of the two-frequency laser beam 100 and the X-Y coordinates so as to form an angle θ (see FIG. 5). After splitting by a beam splitter 190, the signal beam $I_s$ is projected into the multiple scattering medium to be measured. Subsequently, during the process of detecting the optical interference signal of the signal beam $I_s$, the signal beam $I_s$ is split once again by a polarized beam splitter 130 according to the polarization direction, and the mutually orthogonal linear polarized photon pair are respectively detected by photo detectors 140, 150 and signal processors 160, 170, for conversion into heterodyne interference electrical signals, which can be expressed as follows:

$$I_x(\Delta\omega t) = DC + \gamma\cos(\Delta\omega t + \Delta\Phi) \quad (10)$$

$$I_y(\Delta\omega t) = DC - \gamma\cos(\Delta\omega t + \Delta\Phi) \quad (11)$$

By inputting synchronously the two heterodyne interference electrical signals obtained from conversion of the signal beam $I_s$ that penetrated the multiple scattering medium to be measured into a differential amplifier 180, and by subtracting the two signals and amplifying the result for output, a balanced detector can be formed:

$$\Delta I = I_x - I_y = 2\gamma\cos(\Delta\omega t + \Delta\Phi) \quad (12)$$

The output of the differential amplifier 180 is fed to a signal processor 330. At the same time, the reference beam $I_r$ is received by a polarizer 195 and a photo detector 320 from the beam splitter 190, and is subsequently inputted into the signal processor 330 so as to obtain amplitude attenuation and phase delay of the heterodyne interference signals and to enhance the detection sensitivity and signal-to-noise ratio.

Further, as the absorption coefficients $\mu_a$ of hemoglobin in the blood in an oxygenated state ($HbO_2$) and a deoxygenated state (Hb) are obviously different with respect to near infrared wavelengths ($\lambda_1$, $\lambda_2$) (e.g., $\lambda_1$=780 nm, $\lambda_2$=850 nm) (see S. Fantini et al., supra), changes in the hemoglobin saturation($SaO_2$) (see E. L. Heffer et al., supra) in the blood can be obtained in real time from Equations (13)–(16). As relevant theories can be found in the relevant literature mentioned hereinabove, the same will not be explained in detail herein.

$$\Delta\mu_a(\lambda_1) = \varepsilon_{Hb}^{\lambda_1}\Delta Hb + \varepsilon_{HbO_2}^{\lambda_1}\Delta HbO_2 \quad (13)$$

$$\Delta\mu_a(\lambda_2) = \varepsilon_{Hb}^{\lambda_2}\Delta Hb + \varepsilon_{HbO_2}^{\lambda_2}\Delta HbO_2 \quad (14)$$

$$\Delta Hb = \frac{\varepsilon_{HbO_2}^{\lambda_2}\Delta\mu_{2a}^{\lambda_1} - \varepsilon_{HbO_2}^{\lambda_1}\Delta\mu_{2a}^{\lambda_2}}{\left(\varepsilon_{Hb}^{\lambda_1}\varepsilon_{HbO_2}^{\lambda_2} - \varepsilon_{Hb}^{\lambda_2}\varepsilon_{HbO_2}^{\lambda_1}\right)} \quad (15)$$

$$\Delta HbO_2 = \frac{\varepsilon_{Hb}^{\lambda_2}\Delta\mu_{2a}^{\lambda_1} - \varepsilon_{Hb}^{\lambda_1}\Delta\mu_{2a}^{\lambda_2}}{\left(\varepsilon_{HbO_2}^{\lambda_1}\varepsilon_{Hb}^{\lambda_2} - \varepsilon_{HbO_2}^{\lambda_2}\varepsilon_{Hb}^{\lambda_1}\right)} \quad (16)$$

in which $\Delta Hb$, $\Delta HbO_2$, $\Delta\mu_a$ are the variations of concentration of deoxyhemoglobin, oxyhemoglobin, and hemoglobin absorption coefficient, respectively. $\epsilon_{Hb}^{\lambda_1}, \epsilon_{HbO_2}^{\lambda_1}, \epsilon_{Hb}^{\lambda_2}, \epsilon_{HbO_2}^{\lambda_2}$ are extinction coefficients of hemoglobin to different wavelengths $\lambda_1$ and $\lambda_2$ under deoxygenated and oxygenated states, respectively, and are known parameters. The amplitude attenuation and phase delay of DPPDW in the blood can thus be obtained therefrom. Then, $\mu_s'$ and $\mu_a$ of the blood are calculated according to Equations (5)–(9). By utilizing different wavelengths $\lambda_1$ and $\lambda_2$, the absorption coefficients $\mu_a(\lambda_1)$ and $\mu_a(\lambda_2)$ of hemoglobin can be obtained with precision, and the change in hemoglobin saturation in the blood can also be measured in real time. At the same time, an image of the hemoglobin saturation in the blood can also be obtained by using spatial scanning in combination with the solution to the diffusion equation. This invention proposes a novel polarized photon pair near infrared spectroscopy, whereby measurements of the optical characteristics of a multiple scattering medium can be obtained. It is noted that results of experiments conducted by the applicant are shown in FIGS. 6A and 6B, and it was found that the results match the anticipated results of Equations 5 and 6 set forth herein [See Y. H. Chan et al., "The measurement of optical properties of a multiple scattering medium based on diffused photon pair density wave", Advanced Biomedical and Clinical Diagnostic Systems, T. Vo-Dinh, W. S. Grundfest, D. A. Benaron, and G. E. Cohn, Proceedings of SPIE Vol. 4958, 259–272 (2003)]. In summary, by scanning the test object, in combination with the solution to the diffusion equation, the image of the object in a multiple scattering medium can be obtained. Moreover, by using a two-frequency laser source (preferably, two two-frequency lasers) having different center wavelengths, changes in Hb, $HbO_2$ and $SaO_2$, as well as the values of $\mu_s'(\lambda)$ and $\mu_a(\lambda)$ that correspond to different wavelengths, can be measured with precision in real time. In case of a two-frequency, orthogonal linear polarized (or circular polarized) photon pair, rather than a parallel polarized photon pair, propagating in the multiple scattering medium, by having a polarizer located between the scattering medium and the photomultiplier tube, a heterodyne signal can also be generated, and similar results can be achieved. While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

We claim:
1. A method for measuring an absorption coefficient and a reduced scattering coefficient of a multiple scattering medium, comprising the steps of:
outputting a coherent light beam, the coherent light beam including linear polarized P and S wave components having mutually orthogonal polarizations and frequencies $\omega P$ and $\omega S$, respectively;
splitting the coherent light beam into a signal beam and a reference beam, the signal beam and the reference beam including the P wave and S wave components;
projecting the signal beam into the multiple scattering medium;
detecting and converting an optical interference signal of the reference beam and an optical interference signal of the signal beam that penetrates the multiple scattering medium, respectively, into heterodyne interference electrical signals;
comparing the two heterodyne interference electrical signals to obtain amplitude attenuation and phase delay of the signal beam that penetrated the multiple scattering medium; and
inferring the reduced scattering coefficient and the absorption coefficient of the multiple scattering medium at a position where the multiple scattering medium is penetrated with reference to the amplitude attenuation and phase delay thus obtained.

2. The method of claim 1, wherein the coherent light beam is emitted from a linear polarized frequency stabilized two-frequency laser light source.

3. The method of claim 1, wherein the coherent light beam is emitted from a circular polarized frequency stabIlized two-frequency laser light source.

4. The method of claim 1, further comprising a step of concentrating the signal beam to a signal optical fiber prior to projection of the signal beam into the multiple scattering medium; the signal beam that penetrated the multiple scattering medium being detected by means of a detector optical fiber.

5. The method of claim 4, further comprising steps of amplifying and filtering after detecting the optical interference signal of the signal beam that penetrated the multiple scattering medium for conversion into the heterodyne interference electrical signal.

6. The method of claim 1, wherein the splitting step includes a sub-step of generating a photon pair, in which the coherent light beam is passed through a polarizer to become a correlated parallel linear polarized photon pair and a sub-step of beam separation, in which a beam splitter splits the photon pair thus generated into the reference beam and the signal beam.

7. The method of claim 1, further comprising a step of band-pass filtering prior to the step of comparing the heterodyne interference electrical signals, in which a frequency difference of $\omega p$ and $\omega s$ serves as a center frequency for band-pass filtering of the heterodyne interference electrical signal converted from the signal beam that penetrated the multiple scattering medium.

8. The method of claim 1, wherein the step of detecting the optical interference signal of the signal beam that penetrated the multiple scattering medium includes a sub-step of splitting the optical interference signal of the signal beam that penetrated the multiple scattering medium into two mutually orthogonal polarization directions for subsequent detection and conversion into the heterodyne interference electrical signals, and a sub-step of subsequently inputting the heterodyne interference electrical signals into a differential amplifier.

9. A method of imaging a multiple scattering medium, comprising the steps of:
outputting a coherent light beam, the coherent light beam including linear polarized P and S wave components having mutually orthogonal polarizations and different frequencies;
splitting the coherent light beam into a signal beam and a reference beam, the signal beam and the reference beam including the P wave and S wave components;
projecting the signal beam into the multiple scattering medium;
detecting an optical interference signal of the reference beam and an optical interference signal of the signal beam that penetrated the multiple scattering medium for conversion into heterodyne interference electrical signals;

comparing the two heterodyne interference electrical signals to obtain amplitude attenuation and phase delay of the signal beam that penetrated the multiple scattering medium;

inferring a reduced scattering coefficient and an absorption coefficient of the multiple scattering medium at a penetration position;

recording the reduced scattering coefficient, the absorption coefficient and information of the penetration position;

moving the position of incidence of the signal beam and detecting the position of the signal beam that penetrated the multiple scattering medium, and repeating the foregoing steps for a predetermined number of times; and according to the positions of penetration, reconstructing distribution of the reduced scattering coefficients and absorption coefficients of the positions.

* * * * *